United States Patent [19]
Ito

[11] Patent Number: 5,384,028
[45] Date of Patent: Jan. 24, 1995

[54] BIOSENSOR WITH A DATA MEMORY

[75] Inventor: Narushi Ito, Tokyo, Japan

[73] Assignee: NEC Corporation, Japan

[21] Appl. No.: 113,597

[22] Filed: Aug. 27, 1993

[30] Foreign Application Priority Data

Aug. 28, 1992 [JP] Japan .................................. 4-229028

[51] Int. Cl.6 .................................. G01N 27/26
[52] U.S. Cl. .................................. 204/403; 204/406; 204/418; 435/817; 435/288; 435/291
[58] Field of Search ............... 204/406, 403, 416, 418; 435/817, 288, 291

[56] References Cited

U.S. PATENT DOCUMENTS 4,701,253 10/1987 Ligtenberg et al. ................ 204/406
4,909,921 3/1990 Ito ........................................ 204/403

*Primary Examiner*—John Niebling
*Assistant Examiner*—Bruce F. Bell
*Attorney, Agent, or Firm*—Laff, Whitesel, Conte & Saret, Ltd.

[57] ABSTRACT

A biosensor is provided with a memory for storing data including a data and a time of fabricating the biosensor, a lot number of the biosensor, an effective period of the biosensor, the biosensor characteristics, and administrative data of the biosensor. The memory may store additional data such as the measured date, the consecutive (total) measuring time, the measured results, etc.

5 Claims, 7 Drawing Sheets

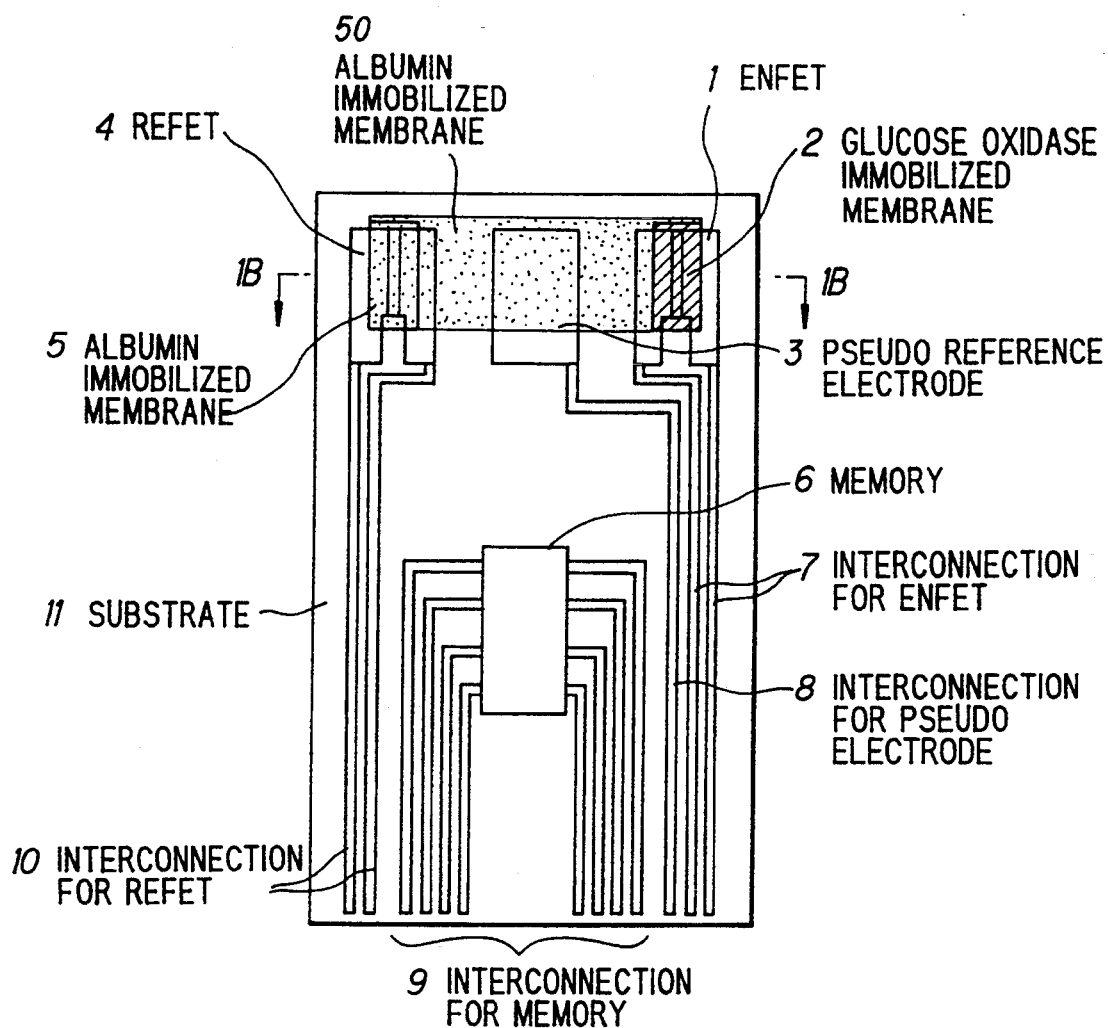

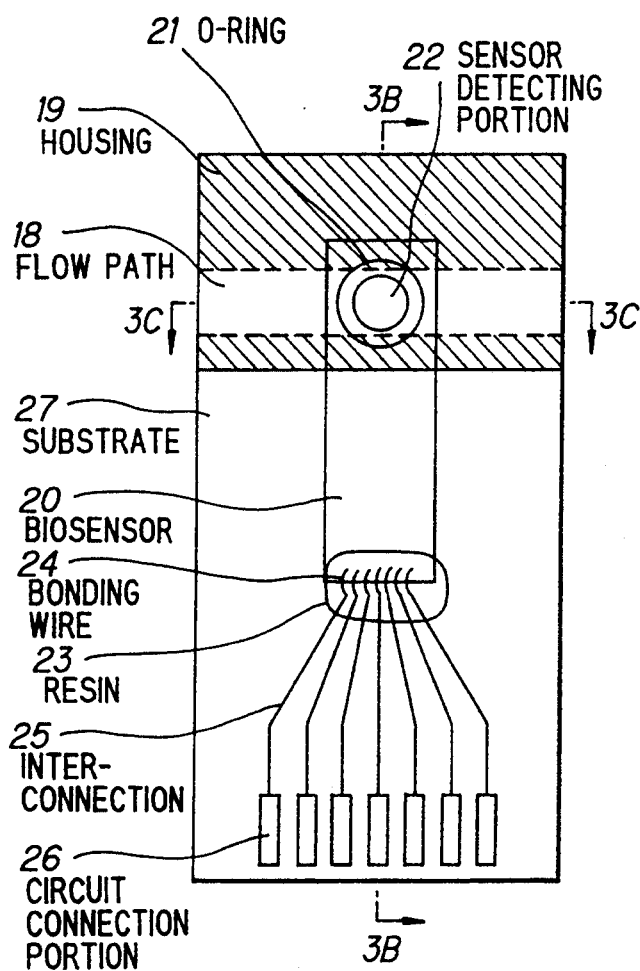
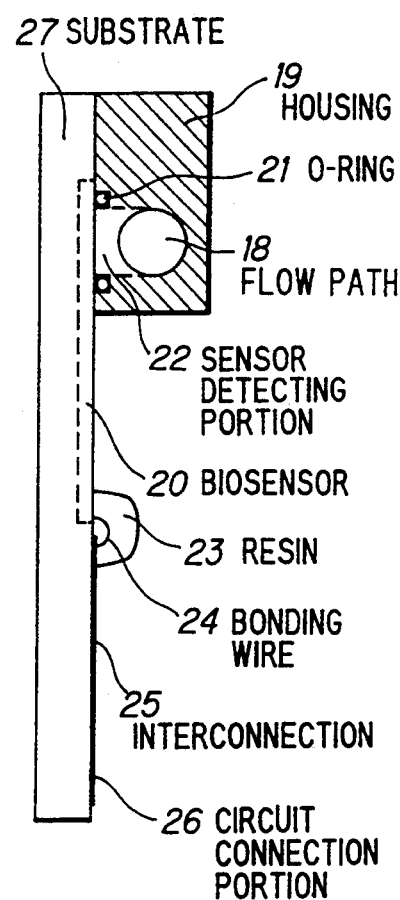
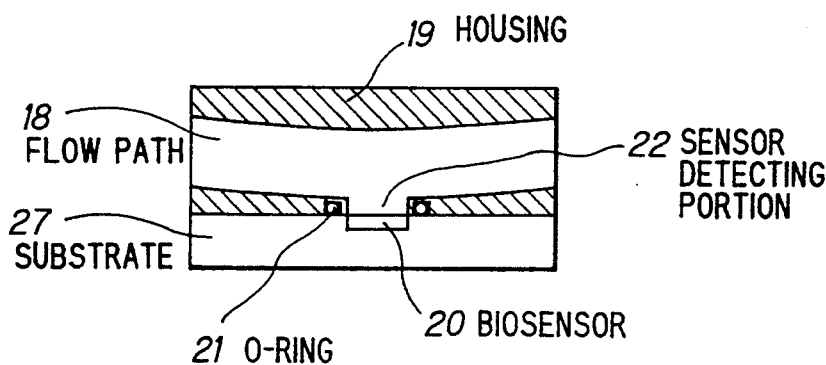

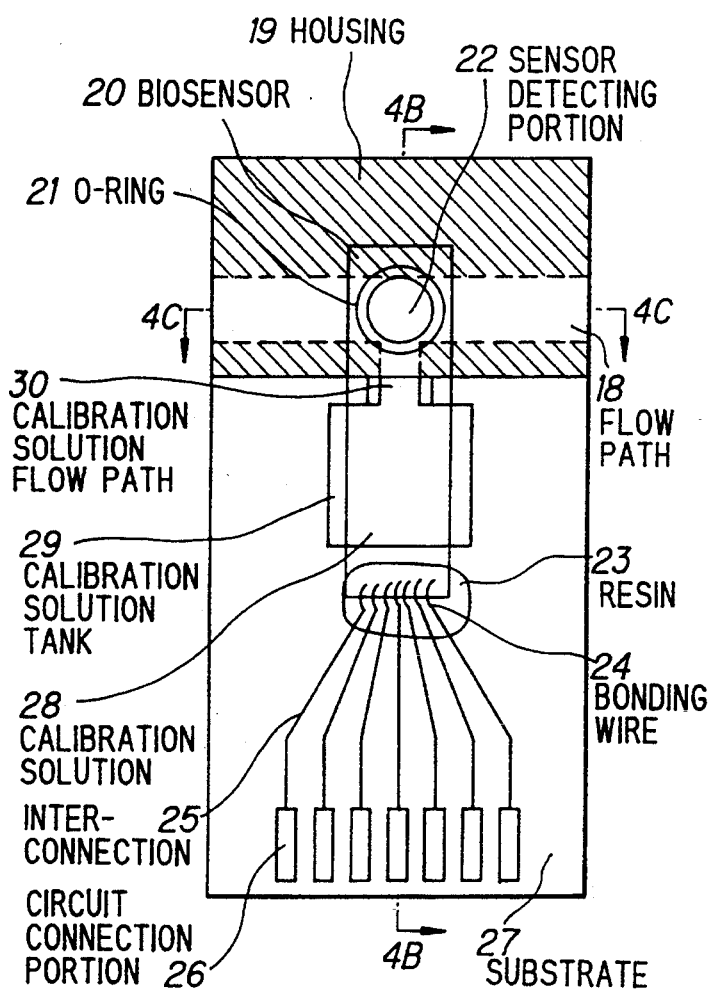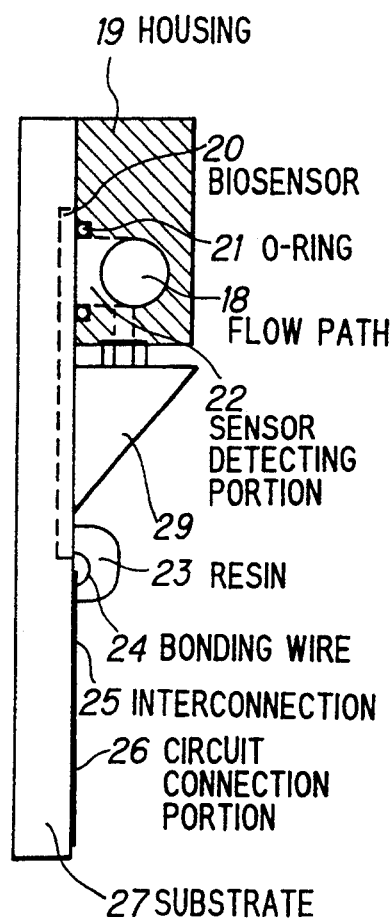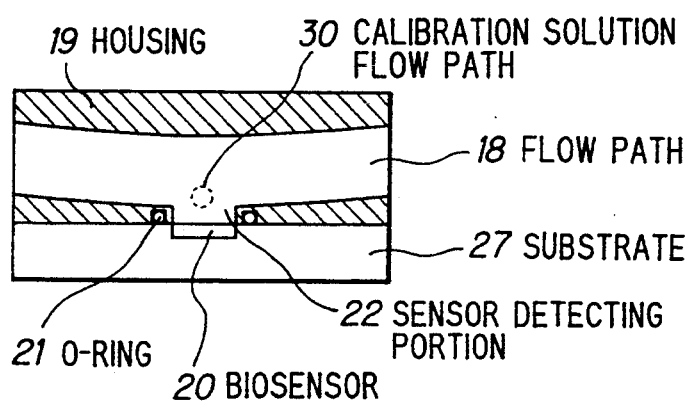

5,384,028

BIOSENSOR WITH A DATA MEMORY

FIELD OF THE INVENTION

The invention relates to a biosensor with a data memory, and more particularly to a semiconductor ion sensor with a memory for measuring a specified organic substance and storing some data including the measured data.

BACKGROUND OF THE INVENTION

In general, components in blood for a human body are measured by using a clinical examination equipment or a biochemical analysis equipment. In a facilitated or simplified blood sugar (glucose) level (concentration) measuring equipment which is used for checking a clinical state of a diabetic, a blood sugar level is measured by coating blood collected needle-stickingly from an ear-lobe or a finger tip of the diabetic on a test paper including enzyme which is thereby change in light absorption degree representing the blood sugar level, as described in "Rinsho Byori, XXIX, 7, page 713, 1981" by Sachiko Kamei, et al., "BME, Vol. 1, No. 11, page 852, 1987" by Akiyuki Okubo, and "Saishin Kansa, Vol. 7, No. 1, 1989" by Hajime Taishi, et al.

A blood sugar level measuring equipment using amperometric biosensor has been proposed these days, as described in "The Lancet, April 4, page 778, 1987", "Kiso-to-Rinsho, Vol., 25 No. 9, page 2877, 1991" by Haruko Shirai, et al., and "Rinsho Kensa Kikie Shiyaku, Vol. 14, No. 3, page 409, 1991" by Hideaki Kurata, et al.

In the measuring equipment, an enzyme field effect transistor (ENFET) and an electrodes are so dipped in solution including sampled blood that a current flowing through the ENFET is changed in accordance with the enzyme reaction of glucose, as well described in the U.S. Pat. No. 4,909,921. Consequently, a blood sugar level can be measure from the change of the current value. The equipment comprises a main unit and a sensor unit, wherein the sensor unit is inserted into the main unit for the calibration of the sensor unit prior to the time of measuring a blood sugar level.

In the calibration of the sensor unit, calibration standard solution is dripped on the ENFET and the electrode, and a series of measuring steps are carried out. In a further calibration of the sensor unit, a correction chip corresponding to a lot number of a sensor included therein is so inserted into the main unit that the sensitivity of the equipment is corrected. In a still further calibration of the sensor unit, correction data is supplied to the main unit in accordance with bar-codes labelled thereon to correct the sensitivity of the equipment.

In the blood sugar level measuring equipment thus calibrated, a blood sugar level of a diabetic is measured, and the measured data is memorized and/or told or reported to a doctor or nurse by the diabetic.

In the conventional blood sugar level measuring equipment, however, there is a disadvantage in that the sensitivity of a sensor is deviated dependent on sensor fabricating conditions and a lot number of enzyme used therein, because the enzyme used therein is biological. Further, there is a disadvantage in that it is required to calibrate a sensor prior to the measurement of a blood sugar level, because the sensitivity of the sensor is lowered during the storage or usage thereof. This calibration is troublesome for the elderly and children. Still further, there is a disadvantage in that measured data is intentionally erased or changed in level by a diabetic, if the data is worse for and/or is not a level to be expected by the diabetic.

SUMMARY OF THE INVENTION

Accordingly, it is an object of the invention to provide a biosensor with a data memory which is not required to be calibrated prior to the measurement of biochemical substances.

It is a further object of the invention to provide a biosensor with a data memory in which measured data is stored.

According to the invention, a biosensor with a data memory, comprises:

a sensor for generating an output dependent on a concentration of an organic substance in solution, the said sensor being provided a sensor substrate; and a memory for storing data of administrating the sensor and said output, the memory being provided on the sensor substrate.

BRIEF DESCRIPTION OF THE DRAWINGS

The invention will be explained in more detail in conjunction with appended drawings, wherein:

FIGS. 1A and 1B are a plan view and a cross-sectional view along the line 1B—1B in FIG. 1A, respectively, showing a biosensor with a data memory in a first preferred embodiment according to the invention, FIGS. 3A to 3C are a plan view, and cross-sectional views along the lines 3B—3B and 3C—3C in FIG. 3A showing a first example of the preferred biosensor mounted on a substrate to be inserted into a measurement main unit, FIGS. 4A to 4C are a plan view, cross-sectional views along the lines 4B—4B and 4C—4C in FIG. 4A showing a second example of the preferred biosensor mounted on a substrate to be inserted into a measurement main unit.

DETAILED DESCRIPTION OF THE PREFERRED EMBODIMENTS

Figure 1B:
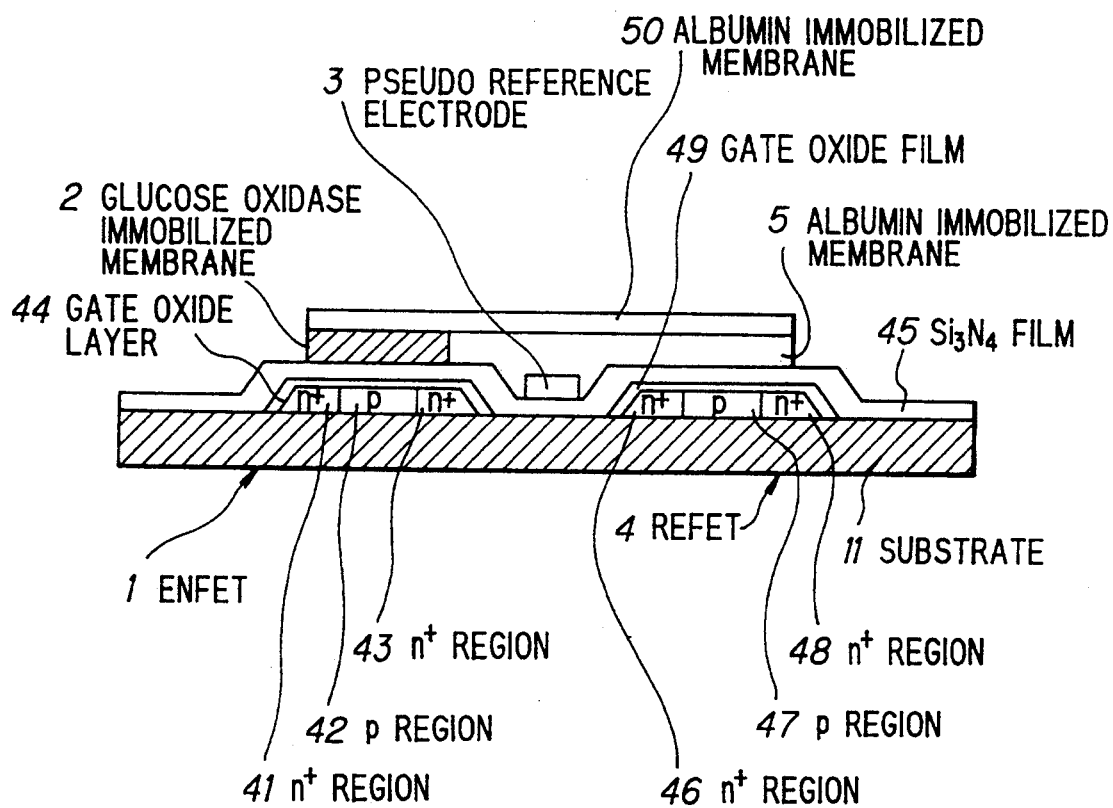

FIG. 1A shows a biosensor with a data memory in a first preferred embodiment according to the invention. The biosensor with a data memory comprises an ENFET 1 having a glucose oxidase immobilized membrane 2 on a gate, a pseudo reference electrode 3 deposited on its surface with Au, a REFET 4 having an albumin immobilized membrane 5 on a gate, and a memory 6, respectively, provided on a sapphire substrate 11. The ENFET 1, the pseudo reference electrode 3, the REFET 4, and the memory 6 have interconnections 7, 8, 9 and 10, as adequately patterned, to be connected to external circuits (not shown).

In the first preferred embodiment, the memory 6 is a flash memory in which contents are totally erased and re-written electrically, and has contents such as a fabricated date of the biosensor, and a lot number, an effective period, characteristics and administrative data of the biosensor which are stored at the time of the fabrication. In use of the biosensor, a date and a time of the measurement being carried out, a consecutive usage period, and measured data are in program stored into the memory 6.

FIG. 1B shows the ENFET 1, the pseudo reference electrode 3, and the REFET 4, respectively, provided on the sapphire substrate 11, wherein the ENFET 1 comprises $n^+$ regions 41 and 43 for source and drain, a p region for channel formation between the source and the drain, a gate oxide film 44 covering the $n^+$ p regions 41 to 43, and the REFET 4 comprises $n^{30}$ regions 46 and 48 for source and drain, a p region for channel formation between the source and the drain, a gate oxide film 49 covering the $n^+$ and p regions 46 to 48. The ENFET 1 and the REFET 4 are covered on the gate oxide films 44 and 49 with a $Si_3N_4$ film, on which the ENFET 1 is provided at a gate with the glucose oxidase immobilized membrane 2, and the REFET 4 is provided at a gate with the albumin immobilized membrane 5. The pseudo reference electrode 3 is also covered with the albumin immobilized membrane 5, and the glucose oxidase immobilized membrane 2 and the albumin immobilized membrane 5 are covered on its top surface with a common albumin membrane 50.

Figure 2:
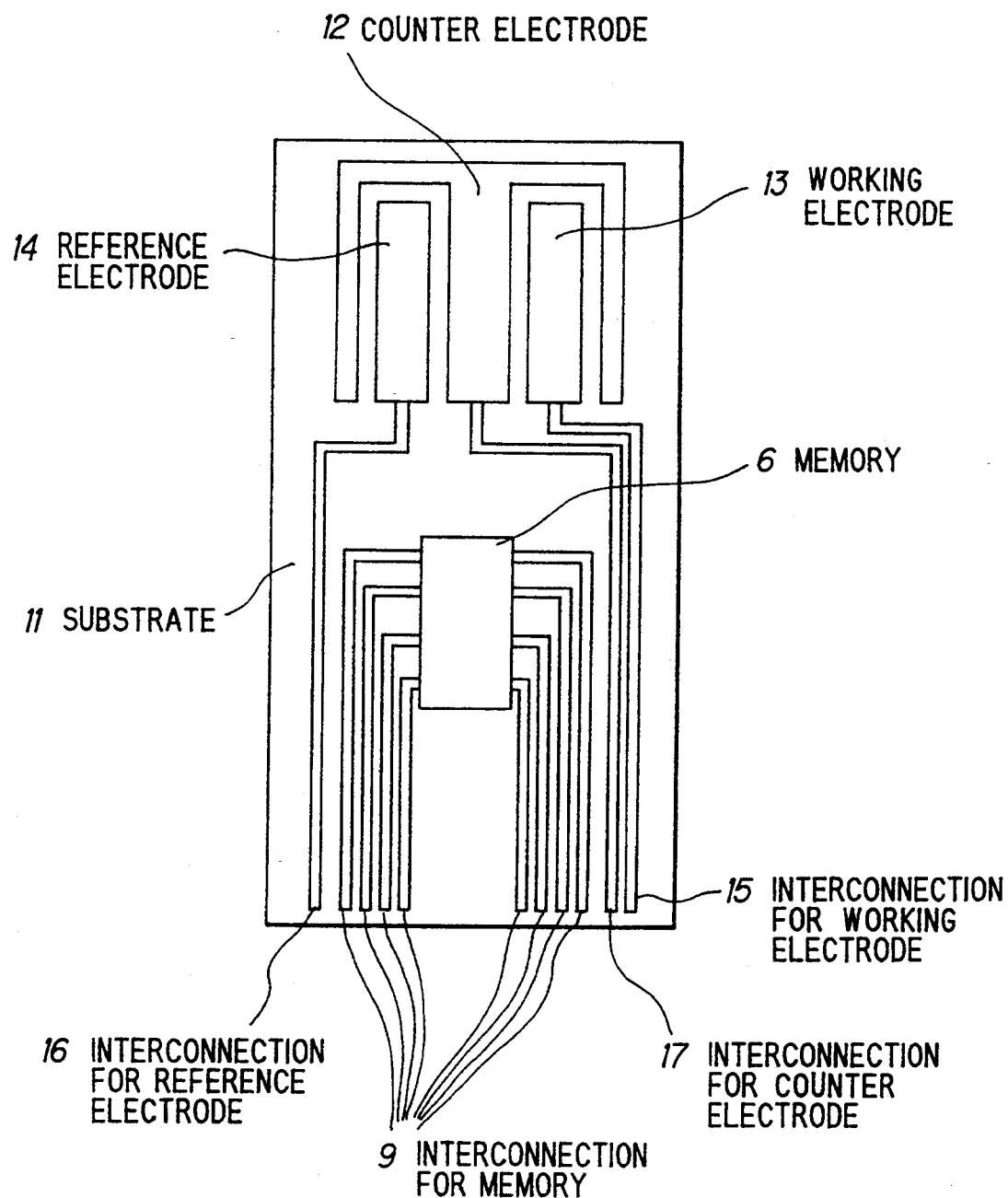
FIG. 2 is a plan view showing a biosensor with a data memory in a second preferred embodiment according to the invention.

FIG. 2 shows a biosensor with a data memory in a second preferred embodiment according to the invention. The biosensor with a data memory is an amperometric lactate sensor which comprises an working electrode 13 and a counter electrode 12 deposited with Au, a reference electrode 14, and a memory 6, respectively, provided on a substrate 11, wherein a lactate oxidase immobilized membrane is formed on the working electrode 13, and an albumin immobilized membrane is formed on the counter electrode 12 and the reference electrode 14. The counter, working and reference electrodes 12 to 14 have interconnections 9, 15 and 17 to be connected to external circuits (not shown), and the memory 6 is a ROM in which a fabrication date of the biosensor, and a lot number, an effective period, characteristics and administrative data of the biosensor are stored.

FIGS. 3A to 3C show the first arrangement in which the biosensor with a data memory (indicated by reference numeral 20) in the first or second preferred embodiment is mounted on a substrate 27 to be connected to a measurement main unit (not shown). The biosensor 20 is placed in a rectangular concave portion of the substrate 27. A sensor detecting portion 22 of the biosensor 20 which is explained as ENFET, REFET and a reference electrode in the first preferred embodiment, and working, counter and reference electrodes in the second preferred embodiment is positioned under a flow path 18 formed in a housing 19 on the substrate 27, and an O-ring 21 is provided around the sensor detecting portion 22 to avoid the leakage of solution therefrom. The sensor detecting portion 22 is connected (via interconnections as shown in FIGS. 1A and 2) to interconnections 25 by bonding wires 24 sealed with mold resin 23, and the interconnections 25 are connected to external circuits in the measurement main unit by circuit connection portions 26.

In operation, the substrate 27, on which the biosensor 20 is placed as explained above, is so inserted into the measurement main unit (not shown) that the flow path 18 is connected to a flow path of the measurement main unit, each electrical element is connected to the circuits in the measurement main unit, and a program stored therein starts to check as to whether the biosensor 20 operates in a normal manner. Then, data stored in the memory 6 of the biosensor 20 is read out therefrom to the measurement main unit, in which a sensor effective period is confirmed, and the calibration of sensor characteristics is carried out. Thereafter, solution supplied from the flow path 18 is dripped on the sensor detecting portion 22 of the biosensor 20 to measure a blood sugar level or a lactate level, and a date and a time of the measurement, a consecutive measuring period, measured data, etc. are stored in the memory 6 of the biosensor 20.

FIGS. 4A to 4C show the second arrangement in which the biosensor with a data memory (indicated by reference numeral 20) in the first or second preferred embodiment is mounted on a substrate 27, wherein like parts are indicated by like reference numerals as used in FIGS. 3A to 3C.

The second arrangement is different from the first arrangement in that it further comprises a calibration-solution tank 29 for containing calibration solution 28, wherein the tank 29 is connected to the flow path 18 of the housing 19 by a flow path 30. The tank 29 is made of a flexible material such as polyvinyl chloride (PVC), so that the tank 29 is easily compressed by a pin (not shown) protruded from the measurement main unit. The pin slides on the tank 29 by means of a sliding mechanism (not shown), so that the tank 29 is compressed to supply calibration solution 28 via the flow path 30 to the flow path 18 for calibration of the biosensor 20, and, when the pin slides off the tank 29, the tank 29 is restored with its original configuration, so that the supply of the calibration solution 28 stops, and air is flown into the flow path 30 to separate the tank 29 from the flow path 18 by a negative pressure generated by the configuration-restoration of the tank 29. Consequently, the cleaning of the sensor detecting portion 22 and the measurement of blood sugar level, lactate level, etc are carried out without any influence from the remaining solution 28 in the tank 29.

Prior to the measurement of a blood sugar level, a lactate level, etc., output signals obtained by using the calibration solution 28 data read from the memory 6 of the biosensor 20 are, in program, processed to correct the sensor characteristics and/or the administrative data. Thus, the biosensor 20 is prepared to start the measurement of a blood sugar level, a lactic acid level, etc. for a patient, etc.

In the second arrangement, although the tank 29 is of a triangular column shape, it may be other configurations such as a circular bellows configuration, and the biosensor 20 is preferable to be used for the measurement of a alcohol level, a uric acid level, etc. for which output signals are deviated in the administration of each lot for biosensors, or the activation is remarkably lowered during the storage of a biosensor.

In accordance with the inventor's experiment, a stand-by to start the measurement is obtained in only two minutes from the insertion of the biosensor-placed substrate 27 into the measurement main unit.

Figure 5:
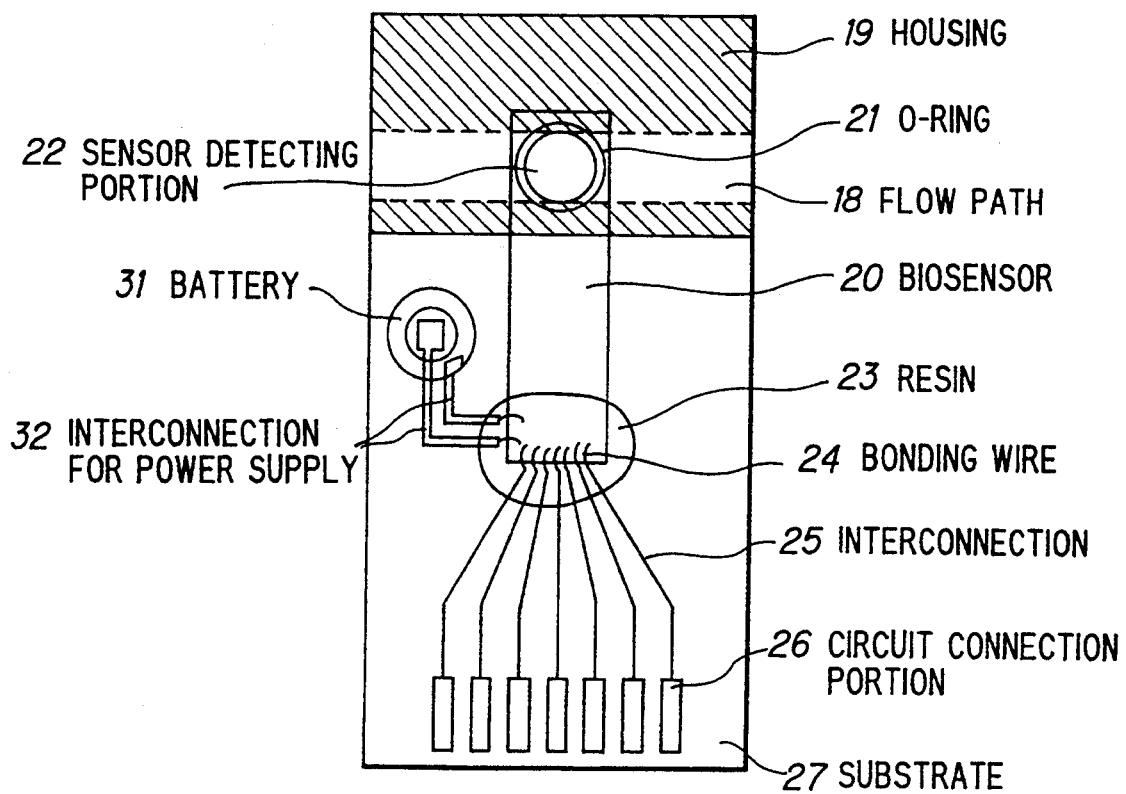
FIG. 5 is a plan view showing a third example of the preferred biosensor mounted on a substrate to be inserted into a measurement main unit.

FIG. 5 shows the third arrangement in which the biosensor with a data memory (indicated by reference numeral 20) in the first or second preferred embodiment is mounted on a substrate 27, wherein like parts are indicated by like reference numerals as used in FIGS. 3A to 3C, and FIGS. 4A to 4C.

The third arrangement is different from the first arrangement in that it further comprises a battery 31 as a power supply, and an interconnection 32 for supplying an electric power from the battery to the biosensor 20.

In the third arrangement, the memory 6 may be of a RAM such as a Static Random Access Memory (SRAM), a Dynamic Random Access Memory (DRAM), etc., because an electric power is supplied to the memory 6.

By using a RAM in the third arrangement, the reading and the writing of data from and into the memory 6 are conducted at a high speed. A large capacity of data is stored and preserved in the memory 6. The advantage is preferably used for a biosensor for the hospital examination which measures a great number of specimens and for a long period of continuous measurement.

In a further arrangement, the biosensor 20 or the substrate 27 may be provided with a quartz oscillation, a pulse counter, and a control circuit. In such a case, the memory 6 can store a history from the fabrication time to the present time and a total measuring time which can be used for the correction of the biosensor 20. Further, such stored data makes it possible to maintain the precision of the measurement, even if the measurement main unit is replaced in the midst of the measurement by a new one.

Figure 6:
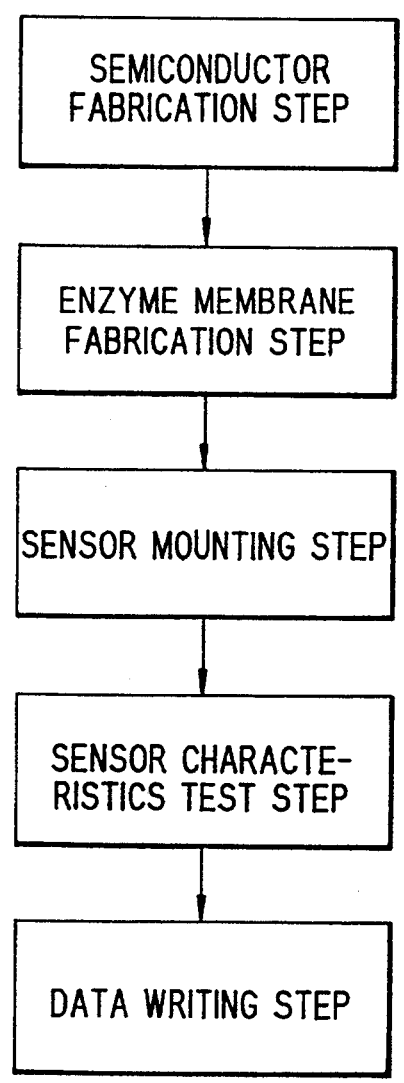
FIG. 6 is a flow chart showing a fabrication process of a biosensor with a data memory in the invention.

FIG. 6 shows a process for fabricating a biosensor with a data memory in the invention.

At the first step ion-sensitive FETs and a memory is fabricated on a common semiconductor substrate by using a conventional memory fabrication step. The memory may be one of ROMs such as EPROM, EEPROM, flash memory, etc. which are programmable, or one of RAMs such as SRAM, DRAM, etc. which require an electric power smaller than that for a ROM. The selection of a memory depends on the use or application of a biosensor.

At the second step, a glucose oxidase membrane is immobilized on a sensor detecting portion, where a glucose sensor is fabricated. The immobilized enzyme membrane is changed dependent on a kind of a biosensor.

At the third step, a sensor thus fabricated is mounted on a substrate.

At the fourth step, the characteristics of a sensor are tested, wherein an ion-sensitive FET such as REFET, ENFET, etc. is checked in operation, and output signals thereof are measured by using calibration solution.

At the final step, the sensor characteristics thus measured, a data and a time of the sensor fabrication, a lot number of the sensor, an effective period, etc. are stored into a memory.

Although the invention has been described with respect to specific embodiment for complete and clear disclosure, the appended claims are not to be thus limited but are to be construed as embodying all modification and alternative constructions that may be occur to one skilled in the art which fairly fall within the basic teaching here is set forth.

What is claimed is:

1. A biosensor with a data memory, comprising:
   an enzyme sensor for generating an output dependent on a concentration of an organic substance in a solution, said enzyme sensor being provided on a sensor substrate with an enzyme membrane; and
   a memory for storing data and calibrating said enzyme sensor wherein the data stored is a fabrication date, and a sensor effective period and wherein said memory is provided on said sensor substrate.

2. A biosensor with a data memory, according to claim 1,
   wherein said enzyme sensor is an ion-sensitive field effect transistor.

3. A biosensor with a data memory, according to claim 1,
   wherein said enzyme sensor comprises first and second ion-sensitive field effect transistors and a reference electrode, said enzyme membrane being immobilized on a gate of at least one of said first and second ion-sensitive field effect transistors, and said first and second ion-sensitive field effect transistors providing a differential output relative to said reference electrode.

4. A biosensor with a data memory, according to claim 1,
   wherein said biosensor is mounted on a substrate and is detachably incorporated into a chemical substance measuring apparatus, said biosensor substrate further comprises a tank having a calibration solution, and a pin for compressing said tank to supply said calibration solution through a flow path of a housing to said enzyme sensor.

5. A biosensor with a data memory, according to claim 1,
   wherein a measuring time and a measuring output of said enzyme sensor are written into said memory.

* * * * *